United States Patent

Lakshminarayanan et al.

[11] Patent Number: 5,933,540
[45] Date of Patent: Aug. 3, 1999

[54] FILTER SYSTEM AND METHOD FOR EFFICIENTLY SUPPRESSING NOISE AND IMPROVING EDGE DEFINITION IN A DIGITIZED IMAGE

[75] Inventors: Arasanipalai V. Lakshminarayanan, Roswell; Khanh Dai Hoang; Richard E. Halbach, both of Alpharetta, all of Ga.

[73] Assignee: General Electric Company, Milwaukee, Wis.

[21] Appl. No.: 08/438,840

[22] Filed: May 11, 1995

[51] Int. Cl.[6] .............................. G06K 9/00; G06K 9/40
[52] U.S. Cl. ..................... 382/260; 382/269; 382/275; 382/128
[58] Field of Search ................... 382/260, 261, 382/262, 263, 264, 265, 266, 275, 274, 128, 304; 358/447, 455, 448, 463, 464, 445

[56] References Cited

U.S. PATENT DOCUMENTS

| | | | |
|---|---|---|---|
| 4,598,372 | 7/1986 | McRoberts | 382/266 |
| 4,736,439 | 4/1988 | May | 382/54 |
| 4,783,753 | 11/1988 | Crimmins | 364/574 |
| 4,827,533 | 5/1989 | Tanaka | 382/54 |
| 4,941,190 | 7/1990 | Joyce | 382/264 |
| 5,003,618 | 3/1991 | Meno | 382/54 |
| 5,023,919 | 6/1991 | Wataya | 382/54 |
| 5,031,227 | 7/1991 | Raasch et al. | 382/22 |
| 5,038,387 | 8/1991 | Sakamoto | 382/54 |
| 5,038,388 | 8/1991 | Song | 382/54 |
| 5,068,909 | 11/1991 | Rutherford | 382/261 |
| 5,073,958 | 12/1991 | Imme | 382/22 |
| 5,101,445 | 3/1992 | Call et al. | 382/54 |
| 5,170,443 | 12/1992 | Todd | 382/58 |
| 5,212,741 | 5/1993 | Barski et al. | 382/51 |
| 5,224,177 | 6/1993 | Doi et al. | 382/54 |
| 5,233,670 | 8/1993 | Dufour et al. | 382/22 |
| 5,271,064 | 12/1993 | Dhawan et al. | 382/54 |
| 5,392,137 | 2/1995 | Okubo | 382/266 |
| 5,557,429 | 9/1996 | Hirose | 358/532 |
| 5,561,724 | 10/1996 | Kido | 382/264 |
| 5,568,572 | 10/1996 | Shu | 382/260 |
| 5,602,934 | 2/1997 | Li | 382/128 |
| 5,610,729 | 3/1997 | Nakajima | 358/463 |

*Primary Examiner*—Jose L. Couso
*Assistant Examiner*—Matthew C. Bella
*Attorney, Agent, or Firm*—Scott A. Horstemeyer; Christian G. Cabou; Phyllis Y. Price

[57] ABSTRACT

A filter system and associated method efficiently suppress noise and improve edge definition in a digitized image. The filter system has a statistical noise determination mechanism which initially determines a baseline noise level of the image. The baseline noise level is used by a filter(s) which operates upon the image data at a later time. After the statistical noise determination mechanism, the filter system generally comprises three independent system branches. Each branch has one or more filters. Each filter is configured to receive an image data array and to modify the image data array to derive a respective modified image data array. Further, each branch has a gain control mechanism adapted to modify a respective modified image data array based upon a gain factor. Finally, an assimilation mechanism combines the modified image data arrays from the gain control mechanisms to derive an improved image data array. Optionally, a rescale mechanism may be employed for adjusting intensities corresponding with pixel values of the improved image data array so that the intensities reside within a predefined range, without degradation in image resolution.

16 Claims, 12 Drawing Sheets

FILTER SYSTEM AND METHOD FOR EFFICIENTLY SUPPRESSING NOISE AND IMPROVING EDGE DEFINITION IN A DIGITIZED IMAGE

BACKGROUND OF THE INVENTION

1. Technical Field

The present invention generally relates to the field of digital data image processing, and more particularly, to a filter system and method for efficiently suppressing noise and improving the edge definition in a digitized image, while providing for extreme flexibility.

2. Related Art

The digital representation of an image through the use of an array of picture element (pixel) values is well known. For instance, medical imaging methods such as magnetic resonance imaging (MRI), ultrasound imaging, computerized tomography scanning (CT), and angiography, and non-medical methods such as radar imaging, all generate raw data which is converted into digitized image data through various mathematical transforms. The digitized image data is most often compiled in a two dimensional array of pixel values, for example, 256×256 pixels or 512×512 pixels in size, each pixel value typically represented by an 8-bit to 16-bit word. The size of the word reflects the precision of the image, e.g., the 16-bit word being more precise than the 8-bit word.

Inherent to all digitized images, regardless of the imaging methodology used, is the presence of noise which degrades the ideal image. The noise present within a digitized image is most often categorized as either high frequency, also known as speckle noise, or low frequency noise. The level of background high frequency noise in an image can affect the observers ability to detect a desired target feature. The detectability of an image feature is directly related to the contrast-to-noise ratio, defined as feature contrast relative to the surrounding image area divided by the noise content of the image. The level of local image contrast and noise content, which defines the contrast-to-noise ratio of the image, is determined in large part by user selectable parameters. For example, with magnetic resonance imaging (MRI), intrinsic tissue parameters, relaxation time $T_1$, relaxation time $T_2$, and proton density, in concert with user selectable image sequencing parameters, such as field-of-view, slice thickness, TE (echo time), and TR (recovery time) determine the noise content and contrast in an image, and therefore, have a direct bearing on the contrast to noise ratio. Therefore, because of the presence of noise, poor edge definition, and low target feature contrast relative to the background noise, the desired target features of a digitized image may not be distinguishable, and the usefulness of the image reduced.

In an effort to reduce the noise and increase edge definition of digitized images, many methods for modifying the image data of these digitized images have been developed. In general, the function of suppressing noise is achieved through the application of a low pass filter which performs a smoothing function on the image data. One such system designed to reduce the noise in a digitized image is disclosed in U.S. Pat. No. 4,783,753 to Crimmins. Conversely, improving edge definition is most often achieved through the application of a high pass filter which performs a sharpening function on the image data. A system designed to increase edge definition is disclosed in U.S. Pat. No. 5,038,388 to Song. Although the functions of reducing noise and sharpening edges are inherently contradictory, many image enhancement methods purport to perform both functions, as demonstrated by U.S. Pat. No. 5,271,064 to Dahwan et al. Additionally, some image enhancement methods purport to attain simultaneous noise reduction and increased edge definition. In this regard, see U.S. Pat. No. 5,031,227 to Raasch et al.

Implementation of any one of the aforementioned image enhancement methodologies is typically accomplished through a pixel-by-pixel analysis, utilizing the pixel value of those pixels within a predefined neighborhood of the pixel to be enhanced. The pixel value that is enhanced is typically increased or decreased as a result of applying several mathematical steps to the image data. The image enhancement methodologies are usually applied globally, whereby each pixel value of the image data is enhanced at least once, and often times more than once through iterative applications of a particular process. Some of the specific types of mathematical approaches taken in modifying digitized image data are a median filter, as disclosed in U.S. Pat. No. 4,736,439 to May, a hulling algorithm, as disclosed in U.S. Pat. No. 4,783,753 to Crimmins, an unsharp masking algorithm, as disclosed in U.S. Pat. No. 5,038,387 to Sakamoto, and an anisotropic filtering using a kernel comprising a matrix of coefficients, as disclosed in U.S. Pat. No. 5,003,618 to Meno.

Although successful to some extent, the methodologies developed thus far are generally complex and computationally intensive, and therefore, do not meet many of the requirements of the marketplace. First, the conventional methods require a great deal of processing time and power. A further disadvantage is the great expense associated with the processing apparatus, particularly the central processing unit. Secondly, in the medical community today, physicians who review the images require not only improved diagnostic capabilities but also an image with an aesthetic appearance which is realistic as well as accurate. However, many of the aforementioned methodologies either introduce artifacts into the image, which were not present in the original image, or remove or alter desired target features which were present in the original image. Lastly, many of the methodologies tend to connect discontinuous linear features within the image, and thereby potentially provide the basis for an inaccurate diagnosis.

SUMMARY OF THE INVENTION

An object of the present invention is to overcome the deficiencies and inadequacies of the prior art as noted above and as generally known in the industry.

Another object of the present invention is to provide a system and method for efficiently suppressing noise and sharpening edges in a digitized image so as to generate an improved image that is aesthetically pleasing and accurate.

Another object of the present invention is to provide a inexpensive system for effectively enhancing digitized images.

Another object of the present invention is to provide a system that improves images and that is computationally efficient.

Another object of the present invention is to provide a system that improves images and that is user-friendly in that it is easy to operate.

Another object of the present invention is to provide a system that improves images and that is highly reliable.

Another object of the present invention is to provide a system and method for suppressing noise and enhancing edges of a digitized image which will not introduce noticeable artifacts such as lines, streaks, or hyper/hypo intense regions not found in the original image.

Broadly stated, the present invention is a filter system and method for efficiently suppressing noise and improving edge definition in a digitized image. The system comprises a statistical noise determination mechanism which initially determines a baseline noise level of the image. The baseline noise level is used by a filter(s) which operates upon the image data at a later time. After the statistical noise determination mechanism, the filter system generally comprises a plurality of independent system branches, three in the preferred embodiment. Each branch has one or more filters. Each filter is configured to receive an image data array and to enhance the image data array to derive a respective modified image data array. Further, each branch has a gain control mechanism adapted to modify a respective modified image data array based upon a gain factor. Finally, an assimilation mechanism combines the modified image data arrays from the gain control mechanisms to derive an improved image data array. The implementation of system branches with corresponding gain control mechanisms in the filter system makes the system extremely flexible and allows for extremely efficient data manipulation.

Optionally, a rescale mechanism may be employed for adjusting intensities corresponding with pixel values of the improved image data array so that the intensities reside within a predefined range, without degradation in image resolution.

The baseline noise level is preferably computed by the statistical noise determination mechanism as follows. A plurality of one-dimensional segments of pixel values corresponding with pixels arranged linearly in the image are acquired. Then, the segments are assimilated to derive the baseline noise level. The foregoing process is desirable in that it requires little data and processing time, and it achieves a confidence level that is sufficiently close to that which would be achieved by a full image scan for noise. As mentioned, the baseline noise level calculated in the statistical noise determination mechanism is used in an area smooth filter situated in one of the system branches.

A preferred organization of the filters is set forth hereafter. A preemphasis filter is employed in a first system branch of the filter system. The preemphasis filter is a nonlinear filter which performs a sharpening function. This filter preferentially alters the pixel values along boundaries and transitions in the image. A boundary is defined as a significant change in pixel value between neighboring pixels. This filter emphasizes the boundaries within the image by contrast enhancement. Used alone, this filter may tend to increase noise. Preferably, preemphasis precedes one of the smoothing filters, such as area smooth or vector smooth, so as to counteract their affect much the same way an equalizer is used on a stereo to compensate for the frequency response limitations of the recording media.

Preferably, two vector smooth filters are employed in a second branch of the filter system. The vector smooth filter is designed to retain linear features within the image. This filter modifies the pixel value of a target or center pixel within a defined window as a function of the mean pixel value along various directional vectors through the center pixel. Hence, the vector smooth filter highlights linear features by means of a directionally weighted smoothing function.

An area smooth filter is employed in a third branch of the filter system. The area smooth filter is a nonlinear filter which reduces local pixel value variations due to noise. This filter employs the tandem application of positive and negative hull procedures. Accordingly, this filter tends to bring up the "target" pixel values that are below, and the "target" pixel values that are above, the pixel values in a defined image neighborhood centered about the target pixel, referred to as a window, so as to reduce speckle noise. Integral to this filter is the baseline noise level of the image as determined in the statistical noise determination mechanism. The area smooth filter involves performing a fill process and a chop process. The basic purpose of the fill process is to smooth peaks. This process modifies the pixel value of a pixel as a function of its ranking with neighboring pixels within a defined window. The purpose of the chop process is to smooth valleys. The chop process is implemented by applying fill to the complement image.

A high enhance filter is also employed in the third branch of the filter system, preferably after the area smooth filter. The high enhance filter is a filter which actually adds preprocessed image data back into the processed image. This filter adds a minimum amount of the original noise back into the modified image making it resemble a high quality unprocessed image so as to remove any artificial appearance resulting from the application of the filters.

In addition to achieving all of the aforementioned objects, the present invention has numerous other advantages, a few of which a delineated hereafter.

An advantage of the present invention is that the filter system suppresses noise and enhances edge definition in a digitized image and can operate in subsecond fashion on an array processor.

Another advantage of the present invention is that the filter system is extremely flexible in that a user can manipulate several gain control mechanisms for fine tuning the appearance of an image.

Other objects, features, and advantages of the present invention will become apparent from the following description when considered in conjunction with the accompanying drawings. All such additional attributes are intended to be included

BRIEF DESCRIPTION OF THE DRAWINGS

The present invention, as described in the claims, can be better understood with reference to the following drawings. The drawings are not necessarily to scale, emphasis instead being placed upon clearly illustrating principles of the present invention. Moreover, in the drawings, like reference numerals represent corresponding parts throughout the several views.

DETAILED DESCRIPTION OF THE PREFERRED EMBODIMENT

Figure 1:
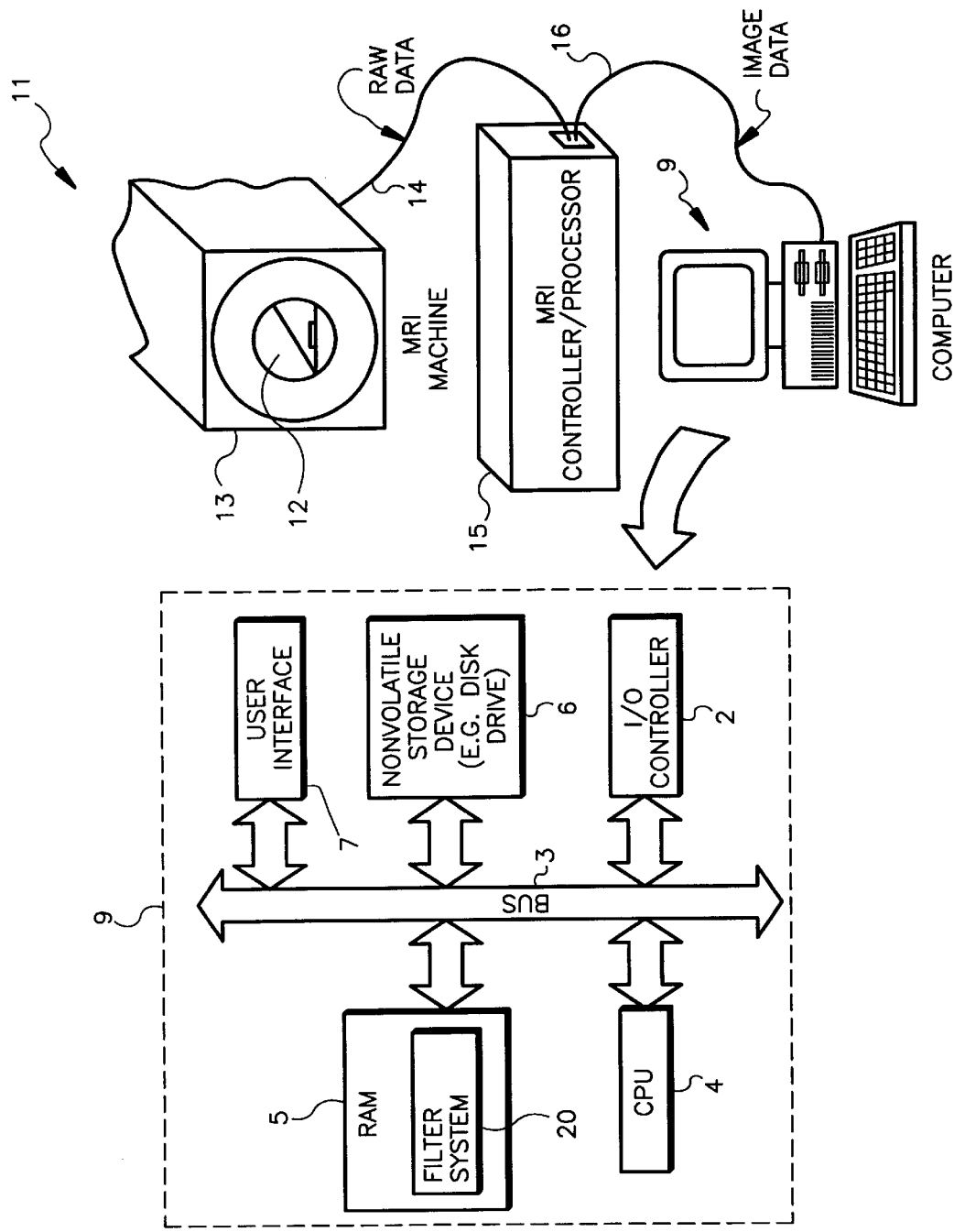
FIG. 1 is a schematic diagram illustrating the filter system of the present invention as applied to, for example but not limited to, magnetic resonance imaging (MRI)

The filter system and method in accordance with the present invention suppresses noise and improves edge definition of a digitized image by using a plurality of filters. A preferred embodiment of the filter system is described hereafter as applied to, for example but not limited to, enhancing magnetic resonance imaging (MRI); however, it will be appreciated by those skilled in the art that the filter system has application to enhancing digital image data derived from other sources and used for other purposes. In fact, the ability to vary the order of the filters of the system, the number of iterations of each filter, and the weighting factors of each filter enables the user to customize the filter system in such a way so as to provide universal application of the present invention to digitized images. Referring to FIG. 1, a MRI system 11 is shown wherein a digitized image of a region of interest is derived by placing a subject in the internal chamber 12 of an MRI machine 13. The MRI machine 13 can be a model HI STAR® MRI machine manufactured by Health Images, Inc., U.S.A., or some other suitable imaging apparatus. Magnetic resonance imaging generally involves the following steps: (1) applying a magnetic field(s) to the subject so as to align the rotational axes of protons in the subject in a preferential direction, (2) modifying the direction of the rotational axes with magnetic gradients and electromagnetic excitation signals (RF signals) in the specific region of interest of the subject, (3) permitting the protons to recover their original orientation so that the protons emit an electromagnetic echo signal, and (4) receiving the electromagnetic echo signal with a receiver. The receiver transfers raw data 14 to a MRI controller 15 for processing. In the MRI controller 15, an image of the specific region of interest is reconstructed via, for example, application of a Fourier transform upon the raw data 14. Following reconstruction of the image, the image data 16 is transmitted to computer 9, for instance, a personal computer.

A novel filter system 20 is preferably implemented by the computer 9 via a software program having a list of executable instructions. However, the filter system 20 can be implemented in hardware, software, or a combination thereof. When in software, as in the preferred embodiment, the various filters of the filter system 20 can be separate software modules in a program. The software modules are stored in memory and applied independently to a digitized image in any desired sequence and with any number of iterations, as prescribed by the computer user.

Referring to FIG. 1, the computer 9 is preferably a general purpose computer having an input/output controller 2. Connected to input/output controller 2 via a bus 3 are a central processing unit (CPU) 4, a random access memory (RAM) 5, and a nonvolatile storage device 6, for example, a hard disk drive mechanism. The operating software for the computer 9 is stored in the nonvolatile storage device 6, while a program for implementing the filter system 20 is stored in the RAM 5. From storage in the RAM 5, a particular software module having a filter is downloaded into the CPU 4 for application upon the input image data 16. The CPU 4 applies the software module filter to image data 16 so as to perform the selected enhancement function on image data 16. Once the particular sequence of software modules (and filters) has been applied to the image data 16, an improved image is produced and stored in RAM 5. The input image 16 or enhanced image 16' produced by the application of the filter system 20 can be displayed to the computer user via the user interface 7, which is typically a printer or a computer monitor for generating a display.

Filter System And Method

Figure 2:
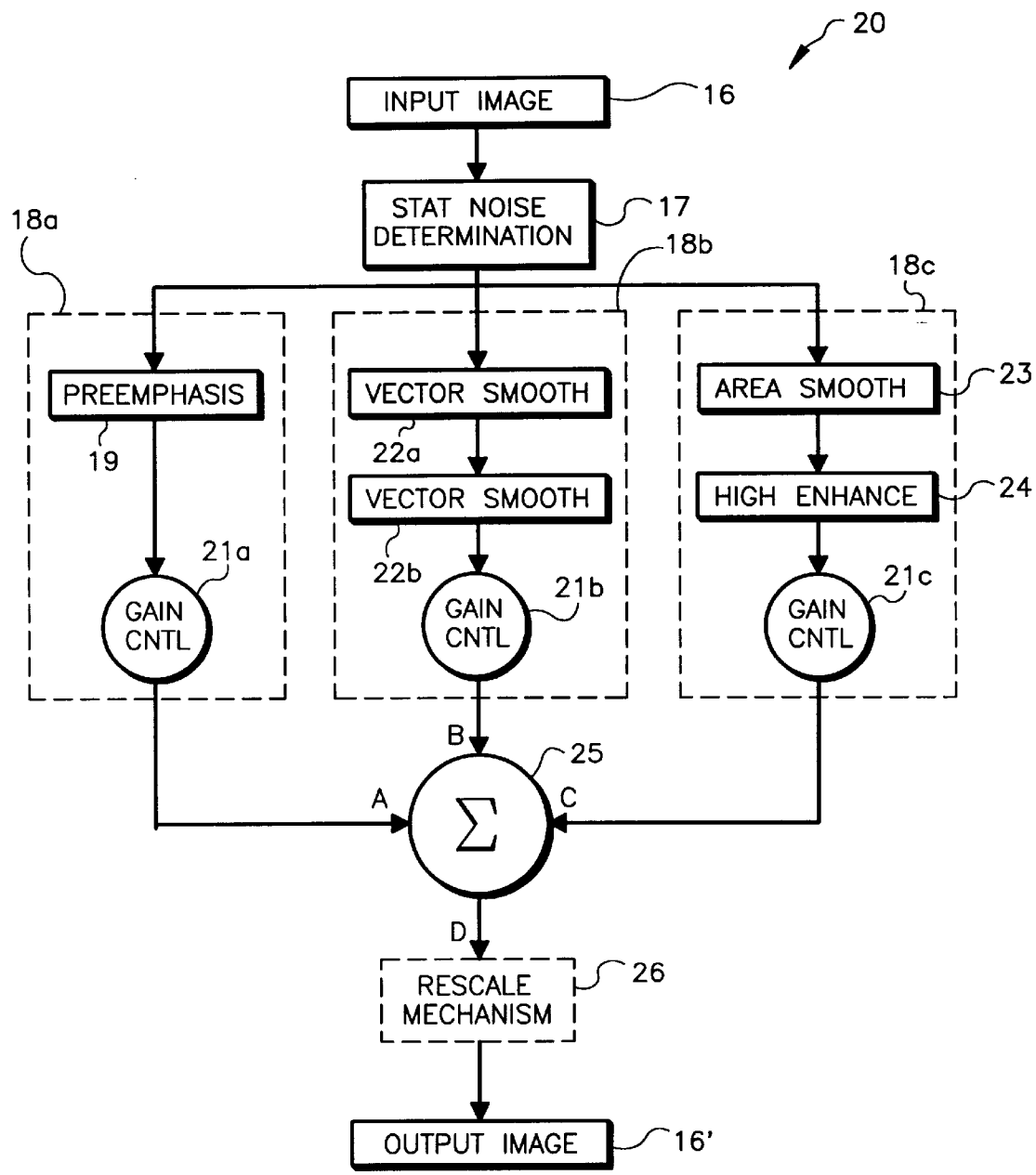
FIG. 2 is a block diagram of the filter system of FIG. 1.

FIG. 2 illustrates a preferred architecture for the filter system 20 and associated methodology of the present invention for processing and improving the appearance of digitized images, including MR images. When enhancing a MR image, the image data 16 of FIG. 2 is first received by the computer 9 (FIG. 1) in the form of a two-dimensional array, or a window, of pixel values. It should be appreciated that the present invention can be applied to a three-dimensional data array by employing a three-dimensional window, such as a 3×3×3 pixel window, when modifying each pixel.

Once the image data 16 has been received, the image data 16 is processed by a statistical noise determination mechanism 17, as illustrated in FIG. 2, in order to determine a baseline noise level. The baseline noise level is utilized in an area smooth filter 23. In the preferred embodiment, the baseline noise level is determined by one of two suitable embodiments (FIGS. 5(A), 5(B)), which will be described in detail hereinafter.

A plurality of filters are configured in parallel to receive and concurrently process a particular array of pixels, after the baseline noise level σ has been established. As shown in FIG. 2, in the preferred embodiment, a particular array of pixel data is communicated to three separate system branches 18a, 18b, 18c by the statistical noise determination mechanism 17. Any number of system branches could be employed, but the implementation of FIG. 2 appears at present to be the best mode for practicing the invention. Each of the system branches 18a, 18b, 18c comprises one or more filters, as will be discussed in detail hereafter. Furthermore, it should be noted that because the statistical noise determination mechanism 17 is positioned before the system branches 18a, 18b, 18c, an area smooth filter 23 may be disposed in any of the branches 18a, 18b, 18c.

The first system branch 18a has a preemphasis filter 19. The preemphasis filter 19 processes the image data array so as to increase edge definition and sharpness. The enhancement factor a is set to about 1.1 and the relaxation factor r is set to about 16 for this application of the preemphasis filter 19. In addition, just as the other filters in the present embodiment, the preemphasis filter 19 utilizes a 3×3 pixel window. After the preemphasis filter 19 operates upon the array to derive modified image data, the modified image data is passed to a gain control mechanism 21a. At the gain control mechanism 21a, the modified image data is changed based upon a gain factor allocated to the particular gain control mechanism 21a. The gain factor of the gain control mechanism 21a, as well as the other gain control mechanisms 21b, 21c described hereafter, may be predefined or it may be adjustable by the computer user.

In the second system branch 18b, the particular image data array is communicated to a first vector smooth filter 22a. The output of the first vector smooth filter 22a is then passed to a second vector smooth filter 22b for further processing. the first and second vector smooth filters 22a, 22b are designed to highlight linear features by way of a directionally weighted smoothing function. In both the vector smooth filters 22a, 22b, a smoothing factor w is set to about 0.8. Moreover, the second vector smooth filter 22b communicates the modified image data to a gain control mechanism 21b. In the gain control mechanism 21b, the modified image data is changed based upon a gain factor allocated to the particular gain control mechanism 21b.

In the third system branch 18c, the image data array is first passed to an area smooth filter 23. The area smooth filter 23 performs a nonlinear smoothing function upon the array in order to reduce local pixel value variations due to noise. In the area smooth filter 23, a smoothing factor w is set to about 0.5, and the iteration variable m is set to about 1.0. The area smooth filter 23 utilizes the baseline noise level σ as determined by the statistical noise determination mechanism 17. Further, the area smooth filter 23 communicates its output to a high enhance filter 24. The high enhance filter 24 restores a specified amount of noise from the original input image 16 back into the image data array. An enhancement factor a of the high enhance filter 24 is set to about 0.3 for this application. Next, the modified image data array is communicated to a gain control mechanism 21c. In the gain control mechanism 21c, the modified image data array is further changed based upon a gain factor allocated to this particular gain control mechanism 21c.

The outputs A, B, C from the gain control mechanisms 21a, 21b, 21c are communicated to an assimilation mechanism 25, where they are mathematically combined (for example, by addition) in order to derive an improved output image D, denoted by reference numeral 16'. The improved output image 16' has less noise than and better edge definition than the input image 16.

In the preferred embodiment, the assimilation mechanism 25 receives a matrix (e.g., 15×15 pixels) of pixel values from each of the gain control mechanisms 21a, 21b, 21c. Moreover, the assimilation mechanism 25 performs the following arithmetic operation upon the matrices:

$$D(x,y)=\Sigma A(x,y)+B(x,y)+C(x,y) \quad (1)$$

The implementation of the gain control mechanisms 21a, 21b, 21c adds extreme flexibility to the filter system 20 and enables easy manipulation by the computer user. Furthermore, the functionality performed by the gain control mechanisms 21a, 21b, 21c may be employed or integrated into the functionality associated with the most previous filter. In other words, for example, the weighting factor associated with the gain control mechanism 21a may be applied to the image data array by the preemphasis filter 19, if desired.

Optionally, a rescale mechanism 26 may be connected to the output D of the assimilation mechanism 25 or employed in the assimilation mechanism 25. In the preferred embodiment, the rescale mechanism 26 is implemented as a component separate from the assimilation mechanism 25, as shown in FIG. 2, and adapted to operate upon the output D from the assimilation mechanism 25. The rescale mechanism 26 essentially monitors the upper and lower limits of the modified image data D and retranslates the modified image data D if the upper and/or lower limits are exceeded, without any appreciable degradation in image resolution.

Figure 3:
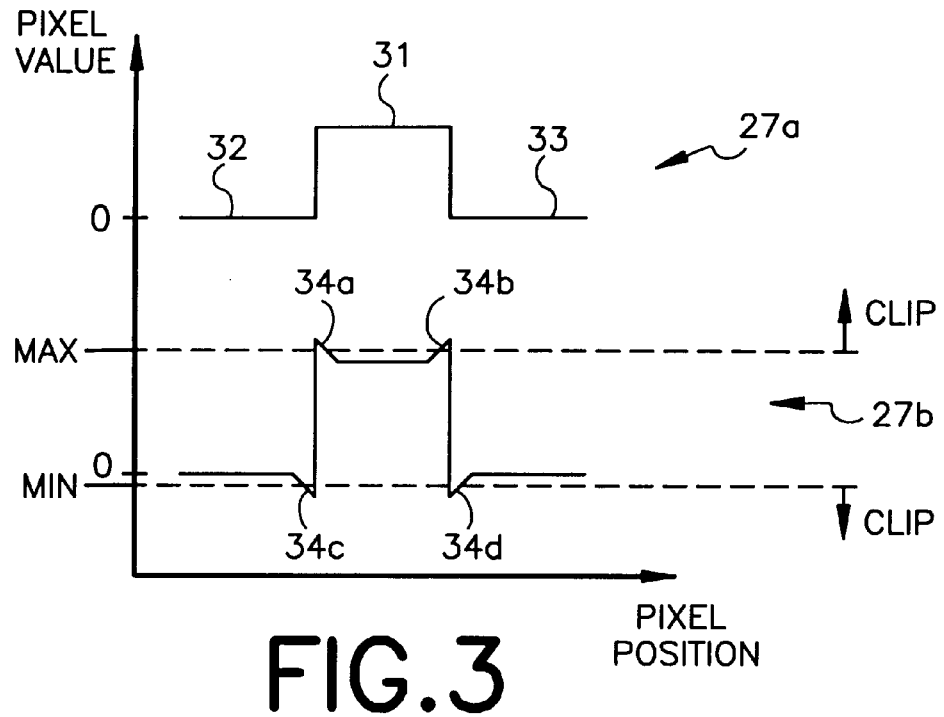
FIG. 3 is a graph of pixel value versus pixel position illustrating a potential clipping hazard associated with the filter system of FIGS. 1 and 2 that is remedied by an optional rescale mechanism shown in FIG. 2.

More specifically, FIG. 3 shows a graph of pixel value versus pixel position in regard to a lineal segment of pixels. Trace 27a illustrates an input image segment wherein a spatial region 31 has a higher pixel value (i.e., brighter) than spatial regions 32, 33. After the input image data 16 has undergone processing by one of the filters 19, 22, 23, 24, particularly the preemphasis filter 19, the input image segment could exhibit a disposition as characterized by trace 27b. As indicated by the trace 27b, the modified segment has pixel regions 34a, 34b that exceed the maximum pixel value limit and pixels 34c, 34d that exceed the minimum pixel value limit of the computer 9 (FIG. 1). Without any readjustment, the pixel values associated with the pixels 34a–34d would be clipped, or purged, and would not appear on a user interface of the computer 9 (FIG. 1). Hence, without any readjustment, valuable data could be lost and resolution compromised.

Figure 4:
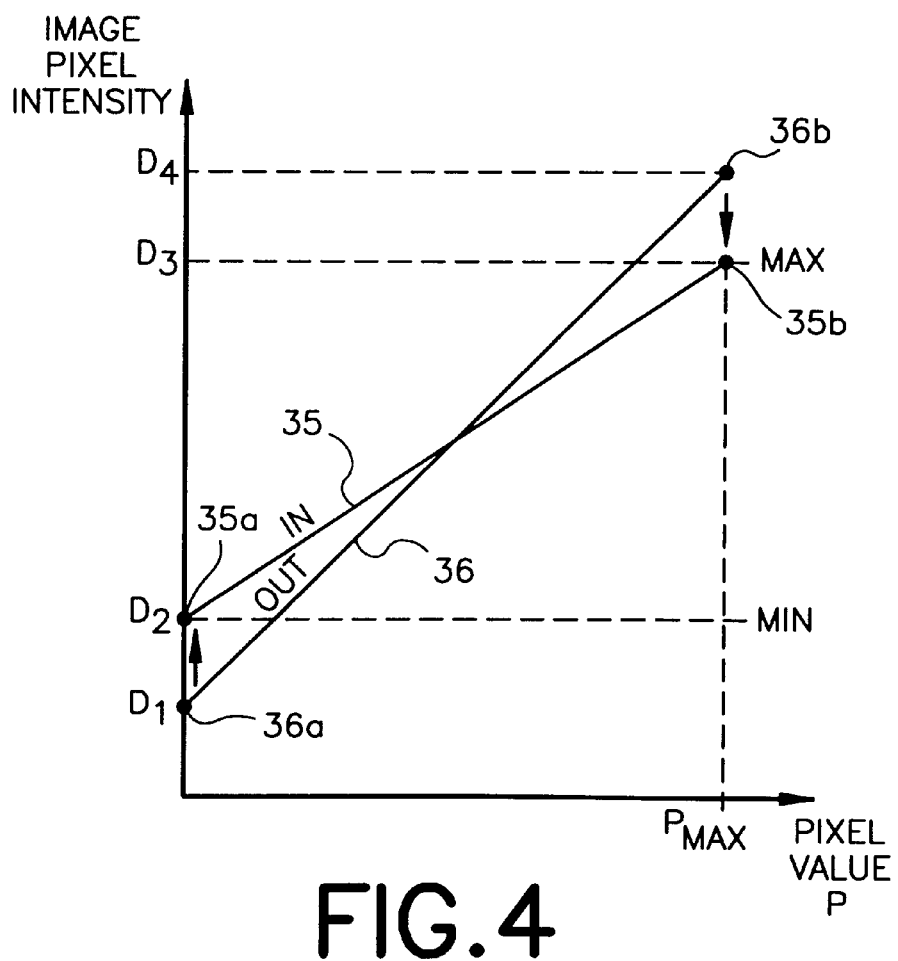
FIG. 4 is a graph of image pixel intensity versus pixel value illustrating the operation and functionality of the rescale mechanism of FIG. 2.

FIG. 4 shows a graph of image pixel intensity versus pixel value and will be utilized to describe the functionality and architecture of the rescale mechanism 26. Line 35 graphically illustrates the distribution of intensities associated with the input image data, and line 36 illustrates the intensity distribution associated with the output image data. The presence of the out-of-bounds pixel values 34a–34d (FIG. 3) results in a much broader range of image display intensities and, therefore, a line 36 having a greater slope and expanse than the line 35. Graphically, the rescale mechanism 26 translates the line 36 into the line 35 by modifying the slope of the line 36 to conform with the slope of the line 35 and by modifying the start and end points 36a, 36b, of the line 36 to correspond with the respective start and end points of the line 35.

In order to accomplish the aforementioned task, the rescale mechanism 26 performs the following mathematical operation upon the image data array D that is communicated from the assimilation mechanism 25 (FIG. 2):

$$P_{new} = P + \Delta P \quad (2)$$

$$\Delta P = (D2 - D1) - P\left[\frac{(D2 - D1) + (D4 - D3)}{P_{\max}}\right] \quad (3)$$

As indicated in equation (2), a new rescaled pixel value $P_{new}$ is computed by the rescale mechanism 26 by adding the unrescaled pixel value P to a resealing factor ΔP. Moreover, the resealing factor ΔP is calculated as indicated in equation (3) based upon the values $D_1$–$D_4$ along the image-pixel-intensity-axis, the maximum pixel value $P_{MAX}$ along the pixel-value-axis, and the unrescaled pixel value P.

Statistical Noise Determination Mechanism

The statistical noise determination mechanism 17 is shown in FIG. 5. It employs a non-iterative statistical process that determines the basic noise properties of the input image 16 for use in a subsequent operation of the area smooth filter 23. The basic noise properties of an image are referred to hereinafter as the baseline noise level σ of the image.

Figure 5A:
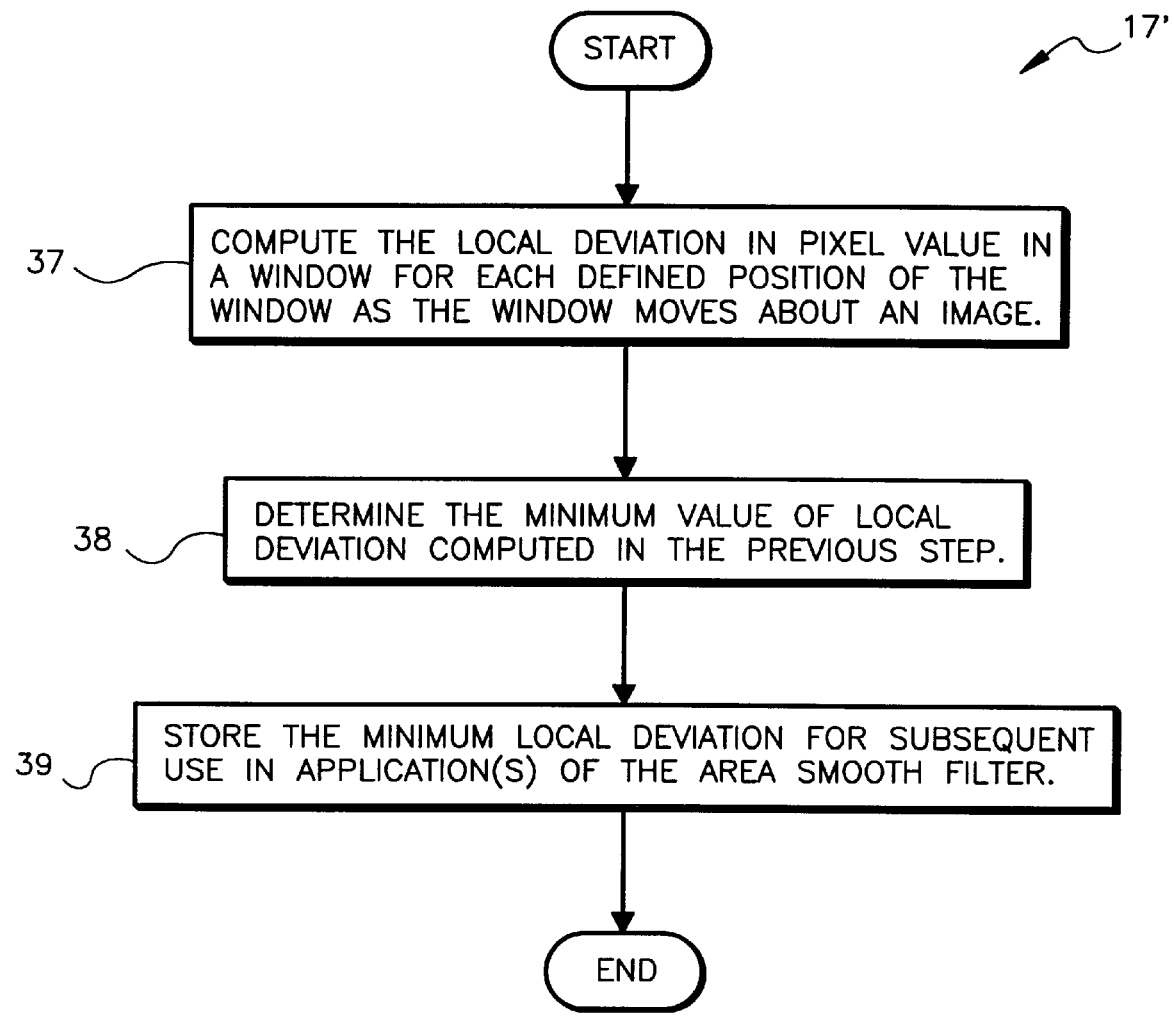
FIG. 5(A) is a block diagram showing the functionality and architecture of a first embodiment of a statistical noise determination mechanism of FIGS. 1 and 2.
Figure 5B:
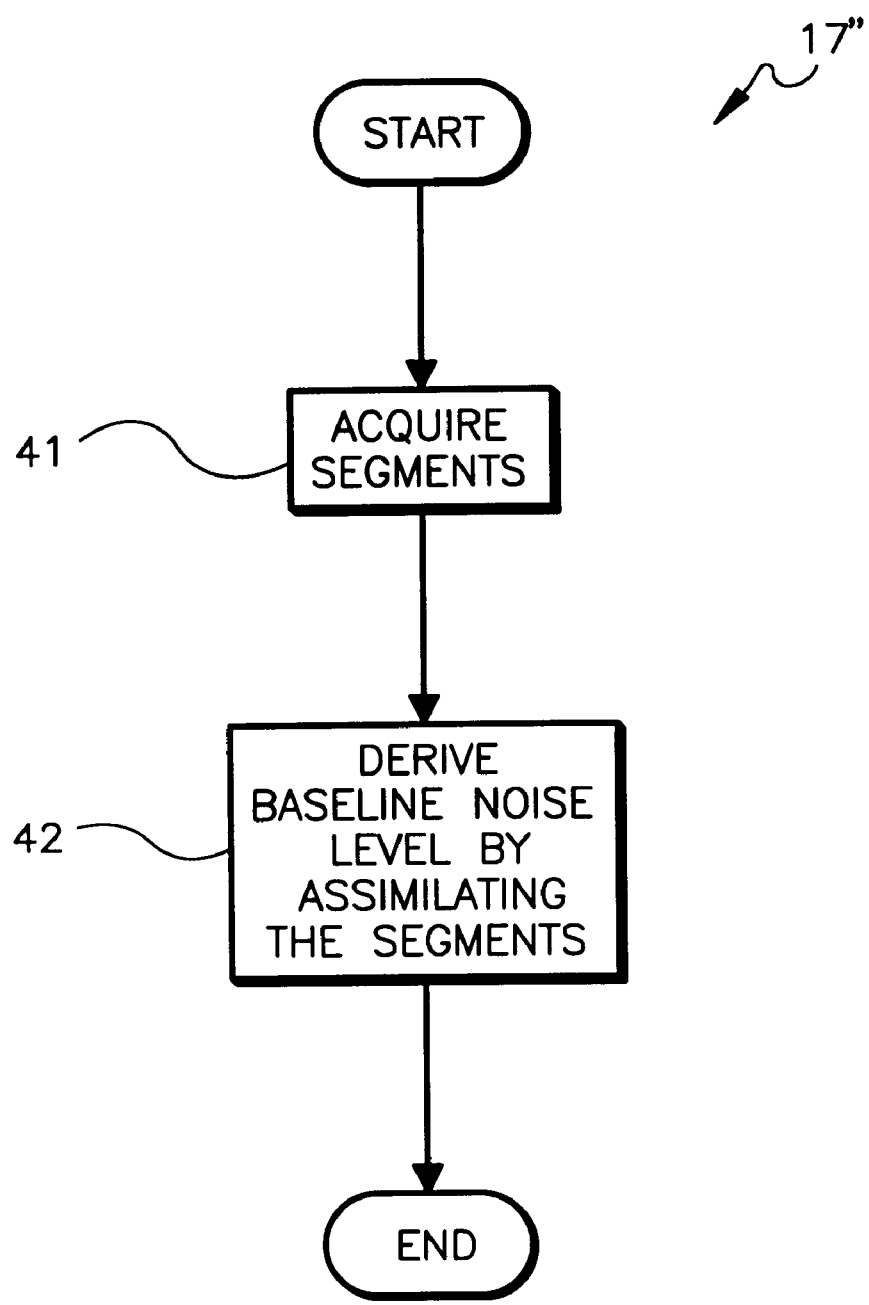
FIG. 5(B) is a block diagram showing the functionality and architecture of a second embodiment of the statistical noise determination mechanism of FIGS. 1 and 2.

The baseline noise level σ can be determined pursuant to a variety of techniques, two examples of which are shown in FIGS. 5(A) and 5(B). FIG. 5(A) illustrates the functionality and architecture of a first embodiment 17' of the statistical noise determination mechanism 17. In the first embodiment 17', the baseline noise level σ is determined by moving a window about the input image 16 and evaluating the pixel values within each window location. For the purpose of simplicity and speed, the first embodiment 17' of the statistical noise determination mechanism 17 typically operates upon a window which is larger than that used in the filters 19, 22, 23, 24, usually 15×15 pixels. The window in the statistical noise determination mechanism 17 also increments itself in larger steps than the filters, 19, 22, 23, 24, typically, seven pixels at a time.

As indicated in block 37 of FIG. 5A, the local deviation of pixel value within each window is determined by subtracting the minimum pixel value within the window from the maximum pixel value within the window, in accordance with equation (4) as follows:

$$\delta_i = M_i - m_i, \quad (4)$$

where $M_i$ is the maximum pixel value in window position "i" and $m_i$ is the minimum pixel value in window position "i." Once the window has completely scanned the image and the local deviation at each window position "i" is computed, it is determined which local deviation represents the minimum non-zero local deviation of all the windows in accordance with equation (5) below, as stated in block 32:

$$\sigma = \min(\delta_i), \quad (5)$$

where variable σ represents the baseline noise level of the input image. The statistical noise determination mechanism 17 should process an image before operation of the area smooth filter 23, because the baseline noise level σ determined in the statistical noise determination mechanism 17 is used in the area smooth filter 23. The minimum local deviation determined in the filter 17 is stored and utilized in the subsequent operation of the area smooth filter 23, as indicated by block 33. Further, it is preferable to employ the statistical noise determination mechanism 17 prior to any filter 19, 22, 23, 24 so that noise level σ is not affected by the modification of pixel values resulting from processing by any filter.

The baseline noise level σ is computed as the minimum peak-to-peak pixel value for the various window positions throughout the input image. The presence of any real signal in the window will almost certainly increase the peak-to-peak pixel difference, so that a window with a smallest peak-to-peak difference will be the window with the least signal and thus the purest estimator of background noise. In almost all cases, the region with the least real signal is likely to be somewhere in the perimeter of the image. Moreover, a significant time penalty is associated with searching the entire interior of the image without improving the noise estimation. Consequently, it is preferable to have the window only scan the perimeter of the input image in the first embodiment 17' of the statistical noise determination mechanism 17.

FIG. 5(B) illustrates the functionality and architecture of a second embodiment 17" of the statistical noise determination mechanism 17. The second embodiment 17" can be performed with much less image data 16, in much less time, and with much less processing support than the first embodiment 17'. In the second embodiment 17", the baseline noise level σ is determined by acquiring a plurality of one-dimensional segments of pixel values corresponding with pixels arranged linearly in the image data 16, as is indicated in block 41. After the segments are obtained, they are assimilated to derive the noise level, as indicated in block 42. Further, the segments may be obtained along a lineal perimeter of the image and/or the segments may be obtained from an internal region of the image. The aforementioned technique is preferred in that it reduces the processing time, as compared to known techniques which usually scan the entire image to derive a noise level, and furthermore, the resultant baseline noise level σ exhibits a statistical confidence level which is not much less than that of the prior art techniques.

Filters

The filters, much like the first embodiment 17' of the statistical noise determination mechanism 17, are applied to input image data 16 by way of a window of a predetermined size which increments itself about the image in an organized raster scan pattern. However, any method of scanning which addresses all of the pixel values in the image can be used. The typical window size for the filters is 3×3 pixels, though there can be circumstances which necessitate a window of different proportions. For example, the vector smooth filter 22 is sometimes implemented with a 5×5 pixel window to better handle noise cluster spots of larger than two pixels.

As the window increments itself about the image, the center pixel at each position of the window is modified as a function of the pixel values of pixels within the window at that position. If the center pixel is located at the border of the image, the rows and columns of pixels about the perimeter of the image are reproduced outside the image's border so that a window positioned about a border pixel is filled with pixels. This pixel replication process at the perimeter of the image is not noticeable on the modified image since only 3 of 8 pixels, for a 3×3 pixel window, or 5 of 14 pixels, for a 5×5 pixel window, of the border pixels are replicated in the window having a border pixel at its center. Once the center pixel of the window has been modified via processing by one of the filters, the window is incremented one pixel so that a pixel adjacent to the previous center pixel is the new center pixel. In a corresponding manner, substantially all the pixels of an image are modified by the application of each filter.

In accordance with the present invention, not all the filters have to be applied to an image and any number and type of filter can be applied to the image data in any of the system branches 18a, 18b, 18c. However, the statistical noise determination mechanism 17 should be applied to the input image prior to the application of the area smooth filter 23 because the area smooth filter 23 uses the baseline noise level σ. Otherwise, the filters can be applied independent of one another and in any order. Furthermore, the vector smooth and area smooth filters 22, 23 can be employed iteratively on image data with each iteration providing further enhancement so as to achieve a specific level of image modification.

Figure 6:
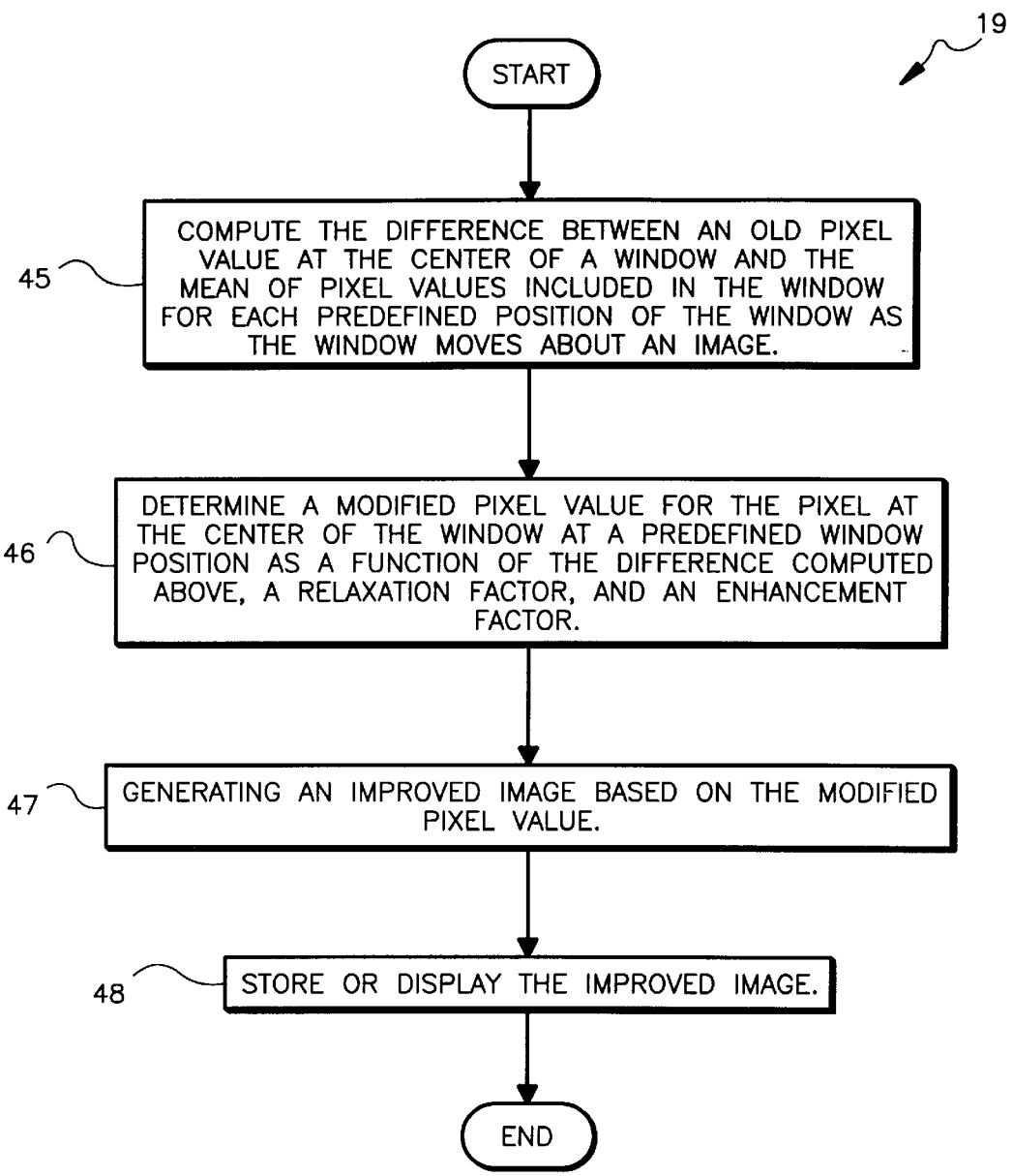
FIG. 6 is a block diagram showing the functionality and architecture of a preemphasis filter of FIG. 2.

The preemphasis filter 19, as shown in detail in FIG. 6, is most accurately described as the preferential modification of pixel values along transitional boundaries, leaving steady state or featureless areas relatively unmodified. As with the statistical noise determination mechanism 17, the preemphasis filter 19 employs a non-iterative process. Two weighting factors associated with the preemphasis filter 19 are the enhancement factor a and a relaxation factor r.

For each window position, a mean pixel value μ within the window is determined, and that value subtracted from the pixel value P of the center pixel as stated in block 45 of filter 19. The resulting value, denoted as d and equal to the difference (P−μ), is used in generating an enhancement argument to be added to the center pixel value P in accordance with equation (6) below, as indicated in block 46 of FIG. 6:

$$P_{modified} = P + \frac{(a*d)}{\left[1 + r*\left(\frac{d}{(P+\mu)}\right)^2\right]} \quad (6)$$

where variable a is the enhancement factor set by the user, variable r is a relaxation factor set by the user, variable $\mu$ is the mean pixel value over the window surrounding the center pixel, and variable P denotes the center pixel value. The above steps are repeated for each pixel in the image as the window is incremented about the image. An improved image can be generated from the modified pixel values and the improved image stored or displayed, as indicated in blocks 47, 48 of the preemphasis filter 19.

Figure 7A:
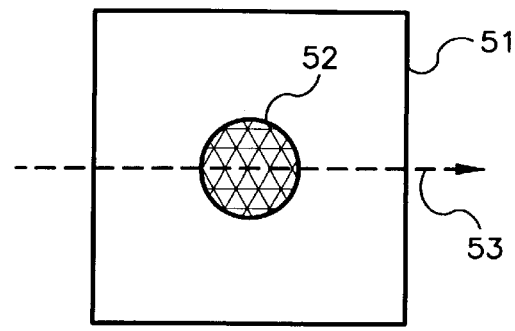
FIGS. 7(A)–7(E) are graphs illustrating the operation of the preemphasis filter of FIG. 6.
Figure 7B:
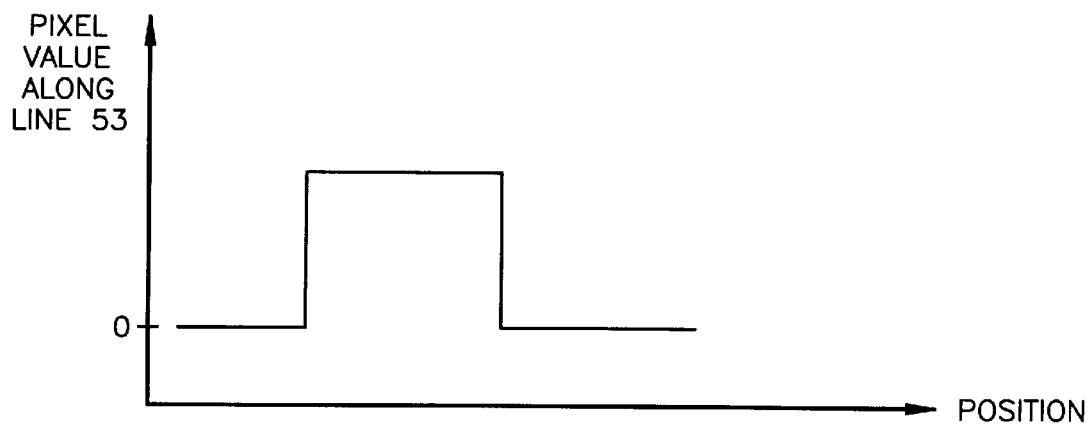
Figure 7C:
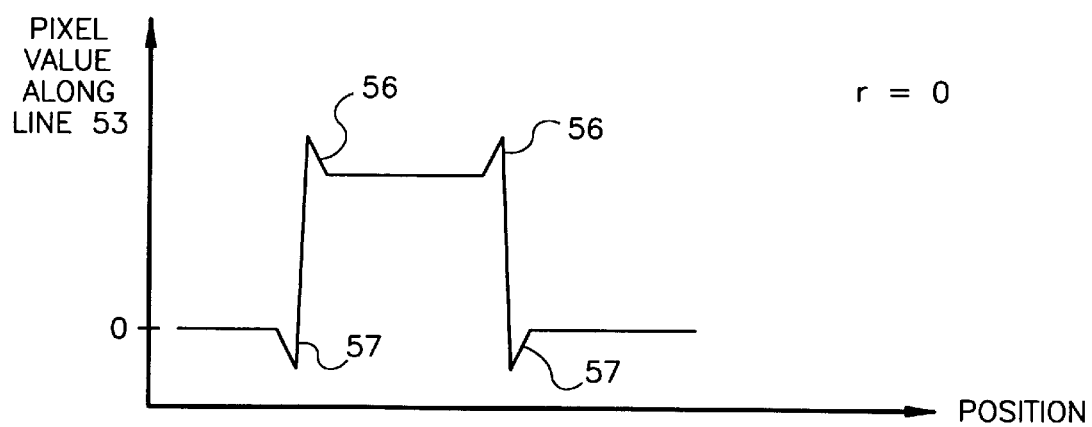
Figure 7D:
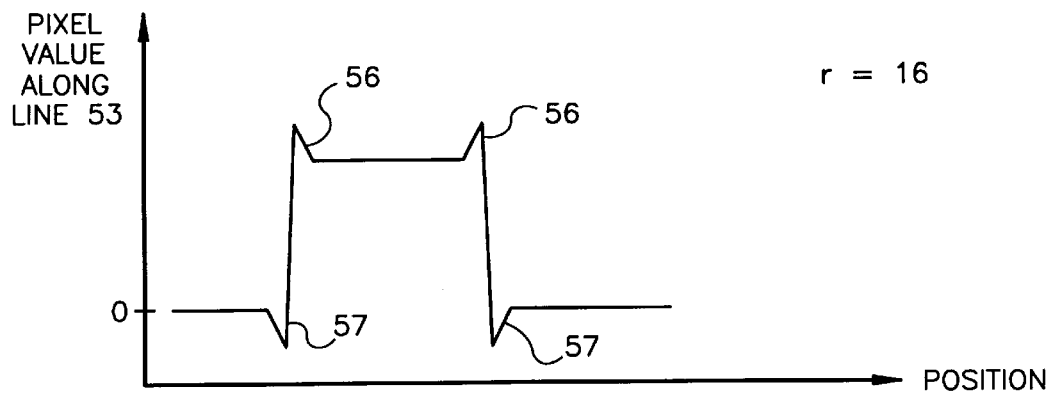
Figure 7E:
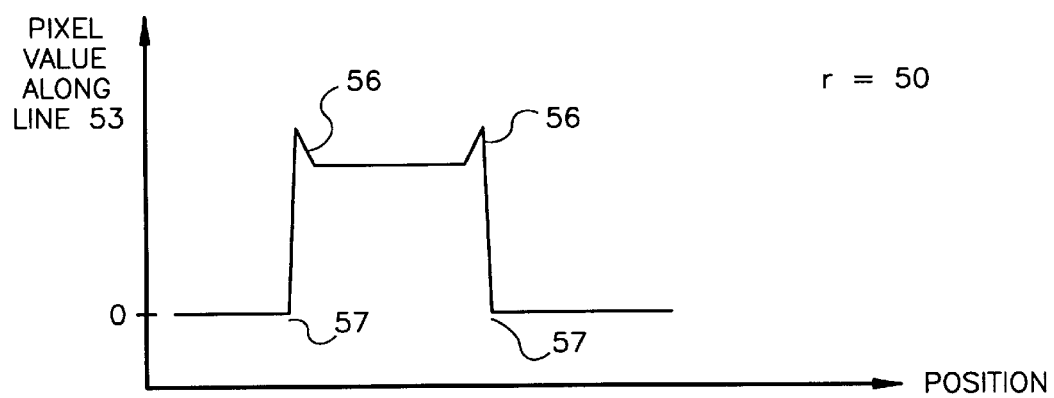

A graphical illustration of the effect of the preemphasis filter 19 on transitional boundaries is depicted in FIGS. 7(A)–(E). FIG. 7(A) is an image 51 having an object 52 at its center and a reference line 53 passing through object 52. FIG. 7(B) illustrates the pixel value of pixels along reference line 53 in FIG. 7(A). Following the application of the preemphasis filter 19, the pixel values along line 53 have been enhanced so as to produce a defined overshoot 56, 57 and thereby increasing edge definition as depicted in FIGS. 5(C)–5(E). As may be derived from equation (6), the greater the value of d, the difference between the center pixel value and the mean of its neighbors, the greater the enhancement argument added by the preemphasis filter 19, i.e. there is a direct relationship between the two. Consequently, in portions of image 51 having no features, i.e. d=0, the pixel values will not change through the application of the preemphasis filter 19. However, the portions of image 51 which do contain transitions or changes in features will be enhanced through the application of the preemphasis filter 19.

In regard to the weighting factors, relaxation factor r modifies the level of the preemphasis filter 19 given to transitional boundaries or features in image areas with low pixel values. This is emphasized in FIGS. 5(C)–5(E) wherein the pixel values along reference line 53 are graphed with r=0 in FIG. 7(C), r=16 in FIG. 7(D), and r=50 in FIG. 7(E). From FIGS. 5(C)–5(E), it is evident that the greater the value of r, the less the enhancement argument at the lower pixel values. However, the enhancement argument at the higher pixel values remain essentially unchanged by variations in r. Additionally, enhancement factor a bears a one-to-one relationship with the enhancement induced by the preemphasis filter 19, as apparent from the enhancement argument added to P in equation (6) above.

Figure 8:
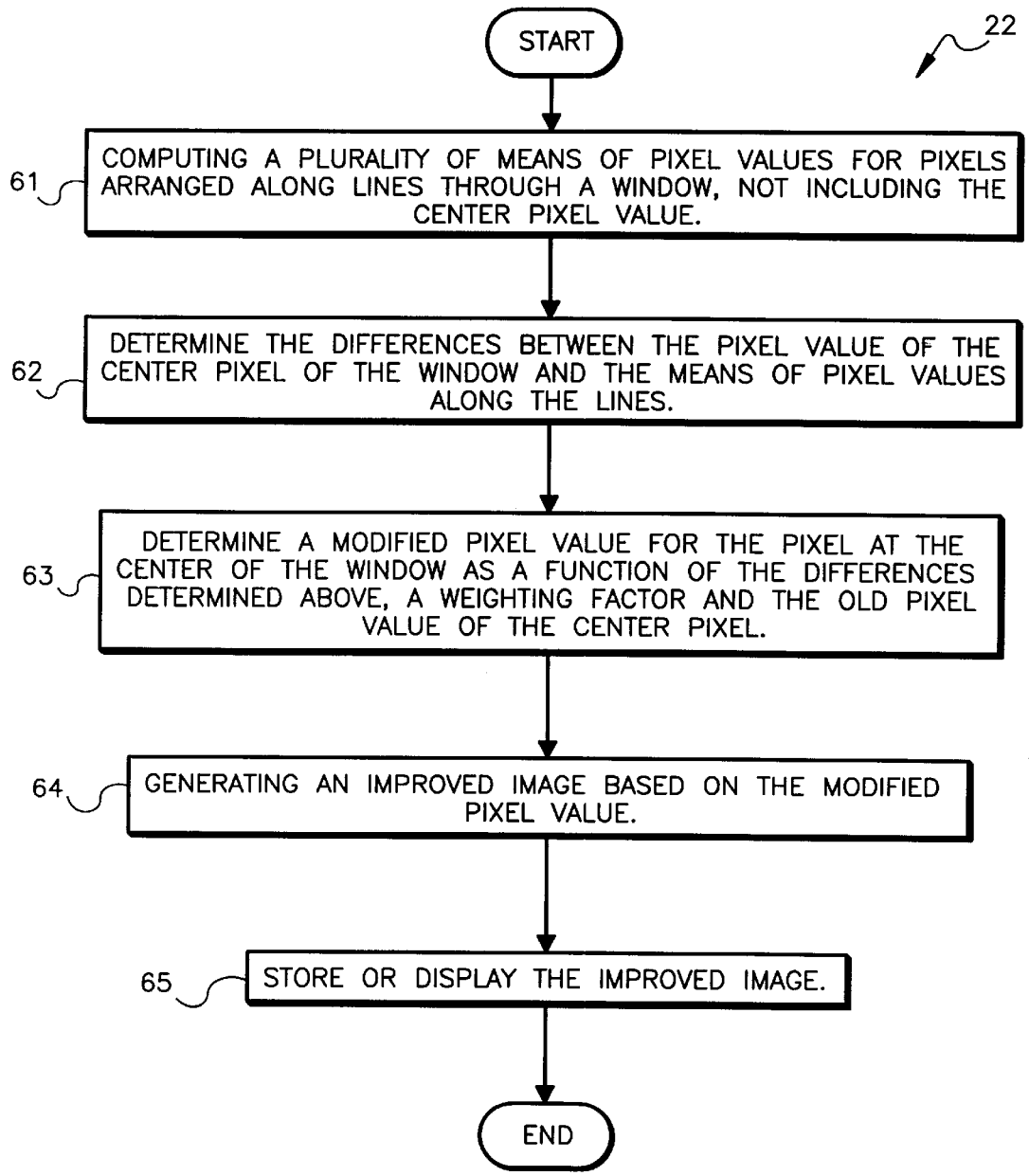
FIG. 8 is a block diagram showing the functionality and architecture of a vector smooth filter of FIG. 2.

The vector smooth filter 22, as shown in detail in FIG. 8, performs a directionally weighted smoothing function by identifying lines/edges and preferentially adjusting the pixel values in the image data 16 so as to follow the intensity of the lines/edges. The vector smooth filter 22 is essentially an iterative nonlinear filter.

Figure 9:
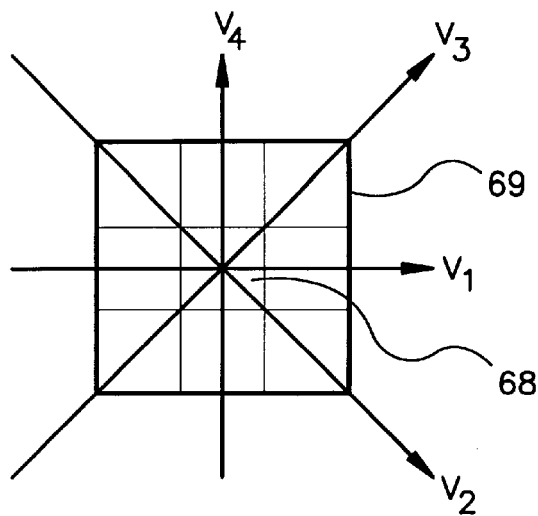
FIG. 9 is schematic illustration of the directional vectors associated with the vector smooth filter of FIG. 8.

As with the preemphasis filter 19, the vector smooth filter 22 employs a window which systematically progresses throughout the image modifying the center pixel for each window position. As applied to each window, the first step of the vector smooth filter 22, as indicated in block 61 of FIG. 8, is to determine the mean pixel value along directional vectors $V_1$, $V_2$, $V_3$ and $V_4$ through the center pixel 68 of window 69, as shown in FIG. 9. Given the mean value along each directional vector, a value d is calculated by taking the absolute value of the difference between the center pixel value and the mean pixel value along each directional vector in accordance with equation (7) below, as indicated by block 62 of filter 22:

$$d_i = |\mu_i - P|, \; i = 1 \text{ to } 4, \quad (7)$$

where "i" corresponds to the particular directional vector $V_i$, variable P is the central pixel value of the window, and variable $\mu_i$ is the computed mean value of all pixels within the window which lie along the direction of the vector $V_i$, excluding the center pixel. A modified pixel value is then computed by adding an enhancement argument to center pixel value P in accordance with equation (8) below, as indicated by block 63 of filter 22:

$$P_{Modified} = P + w\left[\left(\frac{\sum \frac{\mu_i}{d_i}}{\sum \frac{1}{d_i}}\right) - P\right] \quad (8)$$

where P denotes the center pixel value of the window, and w is a smoothing factor set by the user. The smoothing factor w has a one-to-one relationship with the enhancement induced by the vector smooth filter 22. By analyzing aforementioned equation (8), it can be seen that the directional vector with the smallest value of d has the greatest effect upon the enhancement to the center pixel value, and the directional vector with the largest value of d has the least effect. Further, if d equals 0 for any directional vector $V_i$, then the center pixel lies along a line or edge and is not modified. An improved image can be generated from the modified pixel values and the improved image stored or displayed, as stated in blocks 64, 65 of filter 22.

Typically, the vector smooth filter 22 will be implemented using a 3×3 pixel window unless a high percentage of "salt and pepper" noise (i.e. noise spots larger than two pixels) is present, then a 5×5 pixel window is preferable. Large salt and pepper noise can be present with thin slice images or in images of fairly low signal to noise ratio.

Figure 10:
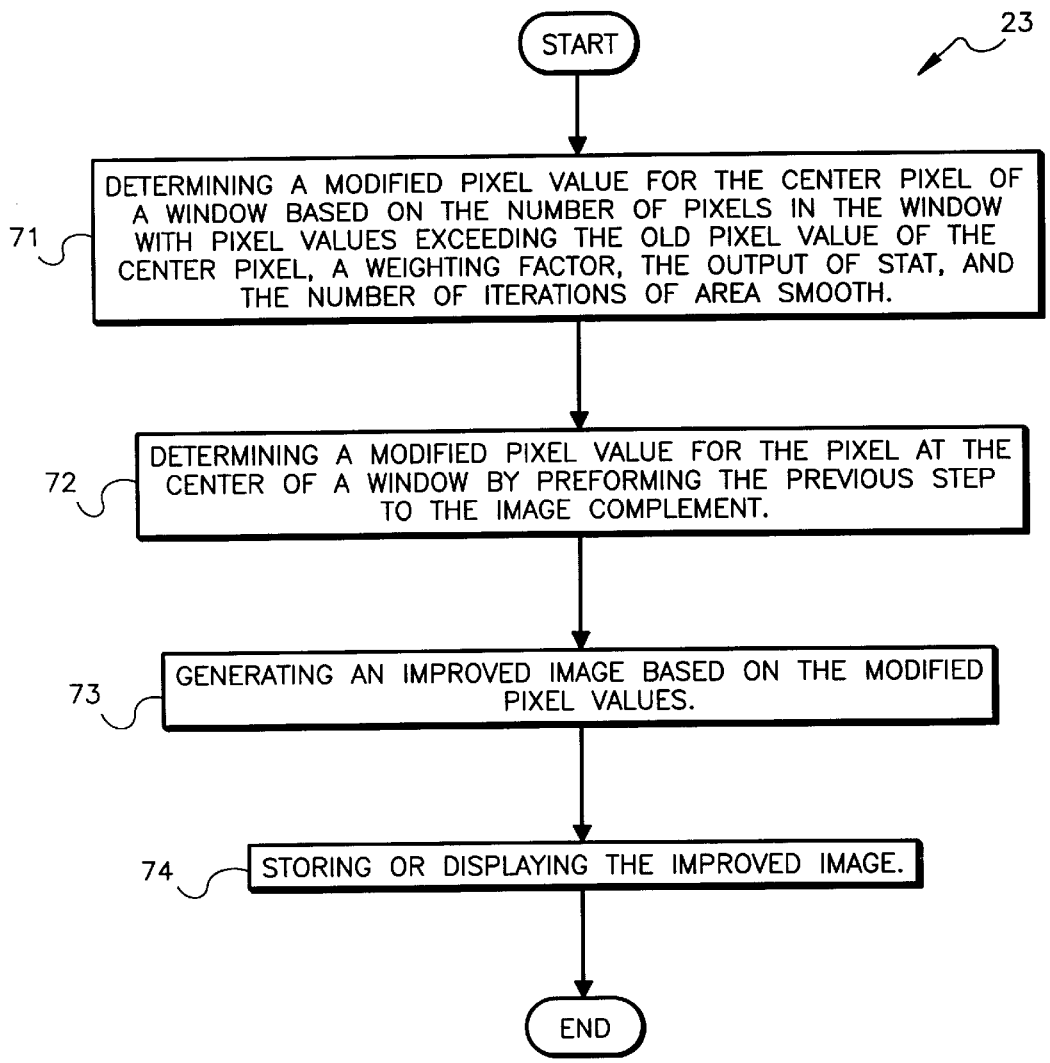
FIG. 10 is a block diagram showing the functionality and architecture of the area smooth filter of FIG. 2.

The area smooth filter 23, as illustrated in detail in FIG. 10, is an iterative nonlinear filter which acts as a non-directional smoothing filter. Each iteration of the area smooth filter 23 involves performing two processes (a) a fill process and (b) a chop process. The fill process is applied to the input image, while the chop process is applied to its complement. The fill and chop processes are essentially identical, but with different inputs. The basic function of fill is to smooth out valleys. Accordingly, when the image is complimented and the chop process performed, the result is the smoothing over of peaks in the image data. The synergistic result of performing both the fill and chop processes is the reduction of speckle noise.

The area smooth filter 23 performs the fill process by modifying every pixel in the image as a function of the pixel's rank within a defined neighborhood of pixels centered about the pixel. The neighborhood is defined by a window typically 3×3 pixels in size. As indicated in block 71 of filter 23, the fill process modifies the center pixel value at a specific window position based upon the number of pixels in the window having a pixel value exceeding the center pixel value. This modification is implemented in accordance with equation (9) as follows:

$$P_{modified} = P + \frac{(k*s*\sigma)}{(m*(n-1))} \quad (9)$$

where variable P denotes pixel value of a center pixel of the window, variable k denotes the number of pixels within the window having a value greater than the center pixel, variable s is a smoothness factor set by the user, variable $\sigma$ is the baseline noise level calculated in the statistical noise determination mechanism 17, variable m is the number of iterations of the area smooth filter 23, and n is the number of pixels in the window. The value of variable s bears a one-to-one relationship with the enhancement argument added to center pixel P induced by the area smooth filter 23. As indicated in block 72, the chop process is performed by modifying the pixel values of the complement image in accordance with equation (9). An improved image can be generated from the modified pixel values and such an improved image stored or displayed, as stated in blocks 73, 74 of the area smooth filter 23.

Figure 11:
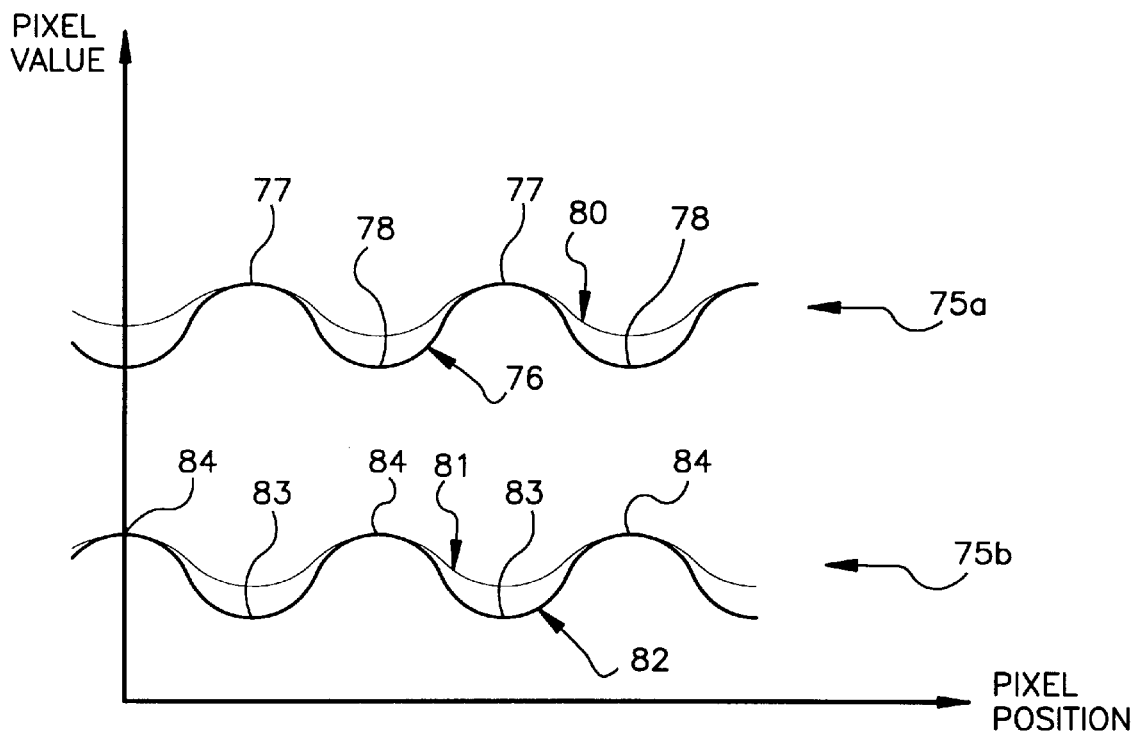
FIG. 11 is a graph illustrating a fill process and a chop process performed by the area smooth filter of FIG. 10.

Referring to equation (9), if very few pixels within the window have a pixel value greater than the center pixel, i.e. k=0, the pixel value of the center pixel will remain unchanged. On the other hand, if virtually all pixels within the window have a value greater than the center pixel value, i.e. k=8, a greater enhancement will be performed on the center pixel value resulting in a significantly modified center pixel value. This concept is illustrated at reference numeral 75a in FIG. 11 as the fill process. In the fill process, the original signal 76 is not modified at its peak values 77 where the pixel values are greater than adjacent pixel values. However, in the valleys 78 of original signal 76, where the pixel values are less than adjacent pixel values, the modified signal 80 is significantly enhanced over original signal 76. Reference numeral 75b in FIG. 11 indicates a similar concept in applying the chop process to the compliment image producing a modified image 81 from complement image 82. As with the fill process, the greatest amount of enhancement occurs when the pixel value of the complement signal 82 is less than those adjacent pixel values, as denoted by numeral 83. Alternatively, complement signal 82 receives no modification at its peak values 84. Thus, it can be seen that the application of the fill process smooths out the valleys, while the application of the chop process smooths over the peaks.

Figure 12:
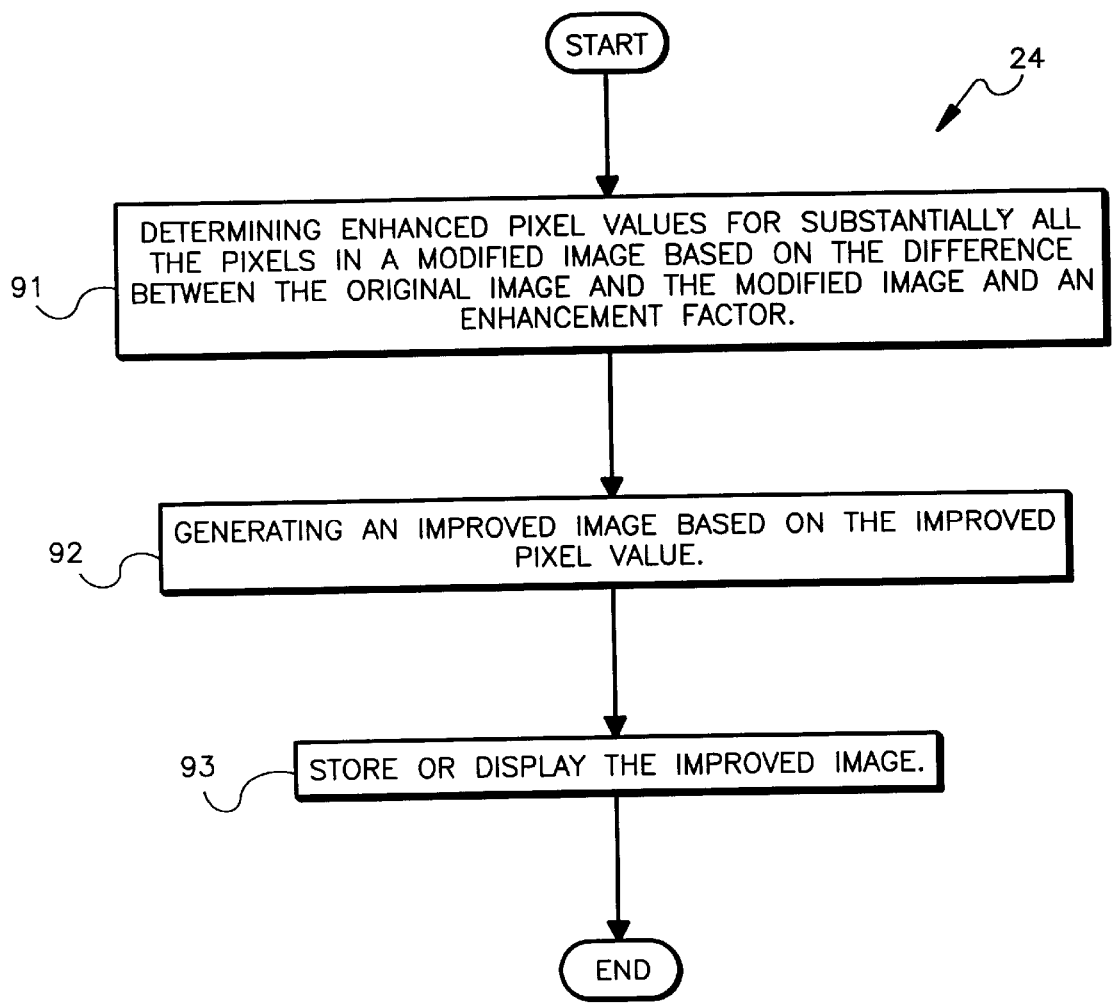
FIG. 12 is a block diagram showing the functionality and architecture of the high enhance filter of FIG. 2.

The high enhance filter 24, as illustrated in detail in FIG. 12, is a non-iterative filter which restores low amplitude, high frequency information back into the image data. Without the application of the high enhance filter 24, all visual image noise is removed, causing a somewhat artificial appearance. Consequently, restoring a minimum amount of the original noise present in the input image data 16 produces an image resembling a high quality unprocessed image, which is more aesthetically pleasing to the computer user. By operation of the high enhance filter 24, pixels within the image are modified in accordance with equation (10) below, as indicated in block 91 of FIG. 12:

$$P_{improved} = P_{modified} + a*(P_{original} - P_{modified}), \quad (10)$$

where variable a is an enhancement factor set by the user, variable $P_{original}$ denotes the original pixel value of the input image, and variable $P_{modified}$ denotes the modified pixel value. An improved image can be generated from the enhanced pixel values and the improved image stored or displayed, as stated in blocks 92, 93 of FIG. 12.

It will be obvious to those skilled in the art that many modifications and variations may be made to the preferred embodiment described above without departing from the novel teachings of the present invention. All such modifications and variations are intended to be incorporated herein and within the scope of the present invention, as set forth in the following claims.

Wherefore, the following is claimed:

1. A method for efficiently improving a digitized image defined by pixel values, comprising the steps of:

supplying a base line of an image, which comprises an image data array, to a plurality of filters, said plurality of filters including a preemphasis filter, a vector smooth filter, and an area smooth filter;

processing and image data array concurrently in said plurality of filters to derive a corresponding plurality of modified image arrays, the preemphasis filter processing the image data array to enhance edges in the image data array, the vector smooth filter processing the image data array to smooth the image data array while emphasizing certain linear features contained within the image data array, the area smooth filter processing the image data array to adjust values of pixels surrounding a target pixel of the image data array such that the pixel values of the pixels surrounding the target pixel are provided with values that are closer in value to the pixel value of the target pixel; and combining said image data arrays to drive an improved image data array.

2. The method of claim 1, further comprising the step of adjusting intensities corresponding with pixel values of said improved image data array so that said intensities reside within a predefined range without appreciably degrading said improved image data array.

3. The method of claim 1, wherein the step of processing the image data array in said area smooth filter comprises the steps of:

(1) selecting a first pixel value to be enhanced in said image data array;

(2) sampling a select group of pixel values within a predefined window surrounding said selected pixel value;

(3) generating an enhancement argument based upon the number of pixels in said predefined window surrounding said selected pixel value of a greater value than said selected pixel value, said baseline noise level of said image, and a smoothness factor; and (4) modifying said selected pixel value based upon said enhancement argument to reduce local variances in pixel values due to noise.

4. The method of claim 3, wherein said step of determining said baseline noise level comprises the steps of:

acquiring a plurality of one-dimensional segments of pixel values corresponding with pixels arranged linearly in said image data array; and assimilating said segments to derive said noise level.

5. The method of claim 1, wherein the step of processing the image data array in said vector smooth filter comprises the steps of:

(a) determining a mean of pixel values for pixels arranged along a line through a center pixel at a center of said image data array;

(b) determining a new pixel value of said center pixel, based on an old pixel value for said center pixel and said mean of pixel values for pixels arranged along said line; and (c) replacing said old pixel value with said new pixel value.

6. The method of claim 1, wherein the step of processing the image data array in the preemphasis filter comprises the step of modifying a pixel value along a transition boundary of said image data array as a function of the difference between said pixel value and the mean pixel value of pixels within a predefined window surrounding said pixel value, a predetermined enhancement factor, and a predetermined relaxation factor.

7. The method of claim 1, further comprising the step of performing a high enhance process in one of said filters, said high enhance process comprising the step of adding noise to said image data array using a user adjustable enhancement factor so that high frequency, low amplitude information is restored in said image data array.

8. A machine having a memory which contains data representing said improved image data array generated by the method of any of claims 1 through 4.

9. A system for efficiently improving a digitized image defined by pixel values, comprising:

a plurality of filters, each said filter configured to receive an image data array and to modify said image data array to derive a respective modified image data array for each of said plurality of filters, said plurality of filters including a preemphasis filter, a vector smooth filter, and an area smooth filter, the preemphasis filter enhancing edges contained in said image data array, said vector smooth filter performing a smoothing function while emphasizing linear features in said image data array, said area smooth filter adjusting pixel values of pixels surrounding a target pixel such that the pixel values of the pixels surrounding the target pixel are provided with pixel values that are closer to the pixel value of the target pixel;

a plurality of gain control mechanisms associated respectively with said filters, each said gain control mechanism adapted to modify a respective modified image data array based upon a gain factor allocated to said gain control mechanism; and an assimilation mechanism in communication with said gain control mechanisms, said assimilation mechanism receiving said modified image data arrays from said gain control mechanisms and combining said modified image data arrays to derive an improved image data array.

10. The system of claim 9, further comprising a rescale mechanism in communication with said assimilation mechanism, said rescale mechanism adapted to adjust intensities corresponding with pixel values of said improved image data array so that said intensities reside within a predefined range without appreciably degrading said improved image data array.

11. The system of claim 9, wherein said area smooth filter comprises:

(1) means of selecting a first pixel value to be enhanced in said image data array;

(2) means for sampling a select group of pixel values within a predefined window surrounding said selected pixel value;

(3) means for generating an enhancement argument based upon the number of pixels in said predefined window surrounding said selected pixel value of a greater value than said selected pixel value, said baseline noise level of said image, and a smoothness factor; and (4) means for modifying said selected pixel value based upon said enhancement argument to reduce local variances in pixel values due to noise.

12. The system of claim 11, wherein said statistical noise determination mechanism comprises:

means for acquiring a plurality of one-dimensional segments of pixel values corresponding with pixels arranged linearly in said image data array; and means for assimilating said segments to derive said noise level.

13. The system of claim 9, wherein the vector smooth filter comprises:

(a) means for determining a mean of pixel values for pixels arranged along a line through a center pixel at a center of said image data array;

(b) means for determining a new pixel value of said center pixel, based on an old pixel value for said center pixel and said mean of pixel values for pixels arranged along said line; and (c) means for replacing said old pixel value with said new pixel value.

14. The system of claim 9, wherein said preemphasis filter is adapted to modify a pixel value along a transition boundary of said image data array as a function of the difference between said pixel value and the mean pixel value of pixels within a predefined window surrounding said pixel value, a predetermined enhancement factor, and a predetermined relation factor.

15. The system of claim 9, wherein one of said filters is a high enhance filter that is adapted to add noise to said image data array using a user adjustable enhancement factor so that high frequency, low amplitude information is restored in said image data array.

16. A system for efficiently improving a digitized image defined by pixel values, comprising:

(a) a statistical noise determination mechanism adapted to determine a baseline noise level from said image;

(b) means for communicating an image data array from said image to first, second, and third branches which are in parallel, each said branch configured to modify said image data array to derive a respective modified image data array;

(c) said first branch having a preemphasis filter, said preemphasis filter adapted to modify a pixel value along a transition boundary of said image data array as a function of the difference between said pixel value and the mean pixel value of pixels within a predefined window surrounding said pixel value, a predetermined enhancement factor, and a predetermined relaxation factor;

(d) said second branch having a vector smooth filter, said vector smooth filter comprising:

(1) means for determining a mean of pixel values for pixels arranged along a line through a center pixel at a center of said image data array;

(2) means for determining a new pixel value of said center pixel, based on an old pixel value for said center pixel and said mean of pixel values for pixels arranged along said line; and (3) means for replacing said old pixel value with said new pixel value;

(e) said third branch having an area smooth filter followed by a high enhance filter, said area smooth filter comprising:

(1) means for selecting a first pixel value to be enhanced in said image data array;

(2) means for sampling a select group of pixel values within a predefined window surrounding said selected pixel value;

(3) means for generating an enhancement argument based upon the number of pixels in said predefined window surrounding said selected pixel value of a greater value than said selected pixel value, said baseline noise level of said image, and a smoothness factor; and (4) means for modifying said selected pixel value based upon said enhancement argument to reduce local variances in pixel values due to noise;

said high enhance filter adapted to add noise to said image data array so that high frequency, low amplitude information is restored in said image data array;

a plurality of user adjustable gain control mechanisms associated respectively with said branches, each said gain control mechanism adapted to independently modify said image data array based upon a gain factor allocated to said gain control mechanism, wherein each said user adjustable gain control mechanism associated by said allocation with each of said branches operates independently of any other of said branches not associated by said allocation therewith; and an assimilation mechanism in communication with said gain control mechanisms, said assimilation mechanism for combining said modified image data arrays from said gain control mechanisms to derive an improved image data array.

* * * * *